United States Patent [19]

Kumano et al.

[11] Patent Number: 4,566,453

[45] Date of Patent: Jan. 28, 1986

[54] VASCULAR ANASTOMOSIS APPARATUS

[75] Inventors: Masafumi Kumano; Ikue Kawashima; Masayuki Hirama, all of Miyagi; Yasuhiro Tsuji, Saitama, all of Japan

[73] Assignees: Tohoku Ricoh Co., Ltd., Miyagi; Chugai Seiyaku Kabushiki Kaisha, Tokyo, both of Japan

[21] Appl. No.: 559,207

[22] Filed: Dec. 8, 1983

[30] Foreign Application Priority Data

Dec. 23, 1982 [JP] Japan .................. 57-224990

[51] Int. Cl.$^4$ .............................. A61B 17/36
[52] U.S. Cl. .................. 128/303.1; 219/121 LA; 219/121 LT; 372/87
[58] Field of Search .............. 372/29, 87, 99; 219/121 LA, 121 LS, 121 LT; 250/205; 350/171, 169, 173; 128/303.1, 395-398

[56] References Cited

U.S. PATENT DOCUMENTS

| | | | |
|---|---|---|---|
| 3,420,719 | 1/1969 | Potts | 219/121 LT |
| 3,710,798 | 1/1973 | Bredemeier | 128/303.1 |
| 3,806,829 | 4/1974 | Duston et al. | 219/121 LA |
| 3,869,680 | 3/1975 | Fletcher et al. | 372/29 |
| 3,874,779 | 4/1975 | Thiel | 350/173 |
| 4,316,467 | 2/1982 | Muckerheide | 128/303.1 |
| 4,470,414 | 9/1984 | Imagawa et al. | 128/303.1 |

Primary Examiner—Kyle L. Howell
Assistant Examiner—Ruth S. Smith
Attorney, Agent, or Firm—Burgess, Ryan & Wayne

[57] ABSTRACT

A vascular anastomosis apparatus using a carbon dioxide laser is proposed. The vascular anastomosis apparatus satisfies three conditions: a long focal distance of not less than 10 cm which is suitable for surgical operations under microscopic observation; a beam spot diameter of 0.1 to 0.3 mm when a laser beam is converged; and a stable, small beam output of not more than 100 mW. A visible guide beam having the same focusing point as that of the carbon dioxide laser beam is used in the vascular anastomosis apparatus.

4 Claims, 15 Drawing Figures

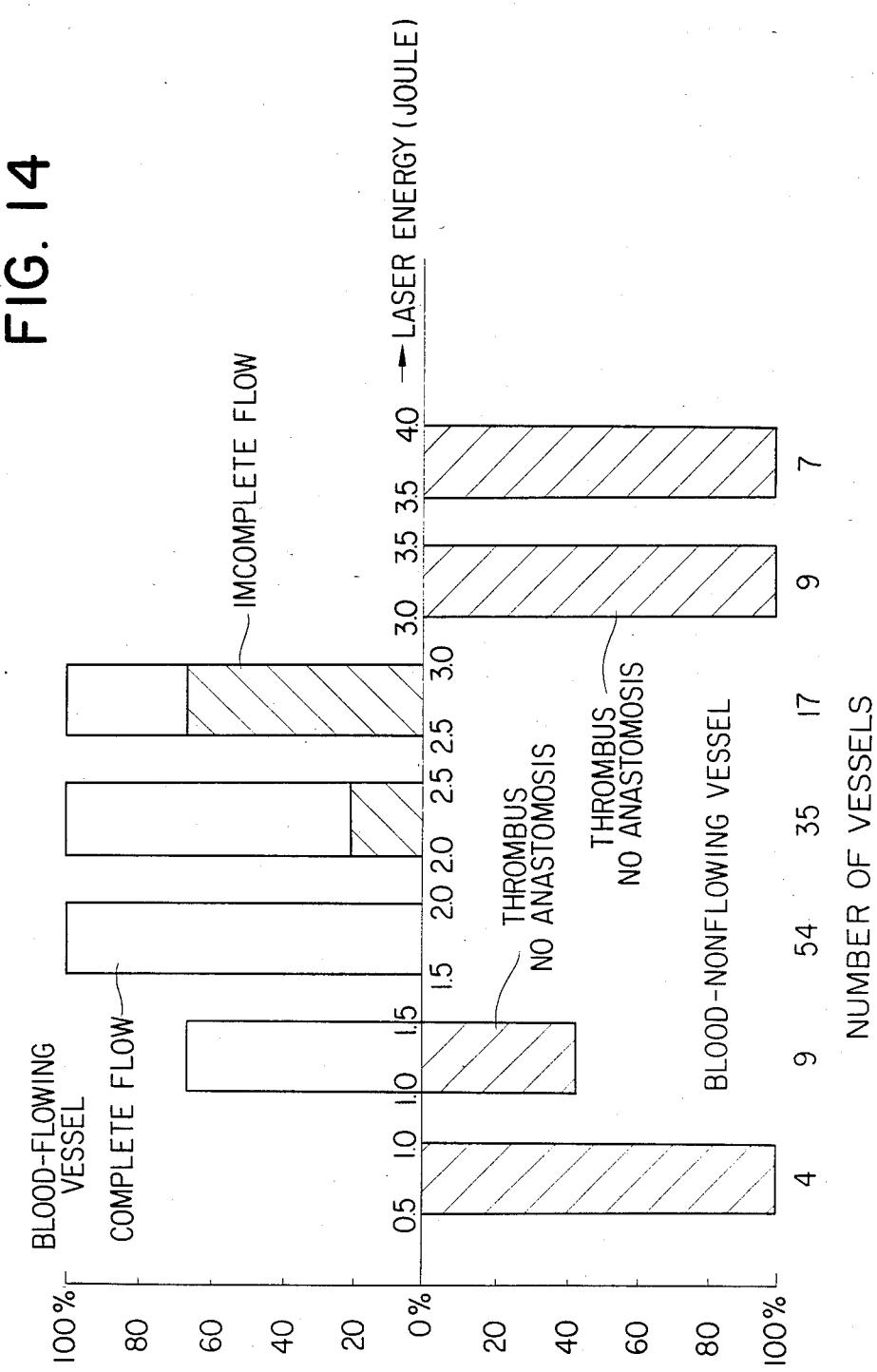

VASCULAR ANASTOMOSIS APPARATUS

BACKGROUND OF THE INVENTION

I. Field of the Invention

The present invention relates to a vascular anastomosis apparatus for anastomosing a blood vessel or the like with a laser beam.

II. Description of the Prior Art

Anastomosis of a blood vessel, a nerve, a lymphatic vessel or the like has been widely practiced in cardiac, cerebral and orthopedic surgery. Conventionally, a needle and thread are mainly used in suturing. However, according to this conventional operation, a small vessel having a diameter of less than 1 mm must be sutured more than 10 times to a portion surrounding the sutured portion of the vessel ends under microscopic observation, so that a highly experienced physician is required. It often takes one hour or longer to complete one suture.

FIG. 1 shows a structure of a blood vessel having an inner layer k, an intermediate layer l, and an outer layer m. When such a blood vessel is anastomosed with a needle and thread suture, the thread extending through the three layers physically damages the blood vessel. Thereafter, after anastomosis is performed, the tissue takes several weeks to recover. Complications such as thrombosis may occur. Also, a space is formed around the anastomosed portion, so that blood leaks from this portion as it flows, and it takes a long time for the blood to coagulate. This occurs typically in arterial anastomosis.

An experiment has been reported wherein optical energy was used to perform anastomosis in order to overcome these problems. The optical energy used was a type of radiation energy, and was expected to leave the organic tissue substantially undamaged as compared with anastomosis using a needle and thread. According to the report (Journal of Microsurgery, 436(1980)) by K. K. Jain, a polyethylene tube was inserted in a blood vessel, and a YAG laser beam was used to irradiate a portion to be anastomosed.

A YAG laser beam has a wavelength of 1.06 μm and its power is fully transmitted to the tissue. This laser beam is not substantially attenuated in power since it is not substantially absorbed in the outer layer of a blood vessel. Therefore, it is considered that the YAG laser beam has the same energy at the inner layer of a blood vessel as at the outer layer thereof. In order to properly anastomose the blood vessel, the energy density of the laser beam at the inner layer thereof must be sufficiently decreased as compared with that at the outer layer thereof. This indicates that the laser beam must be focused on the outer layer by using an optical system having a short focal length. As a result, the operational procedures become time-consuming, and a highly experienced physician is required, resulting in inconvenience.

The mechanism of anastomosis using optical energy is not yet completely understood, but it is considered that collagens contained in the blood vessels melt and adhere to each other. This indicates that the laser beam is used as thermal energy. From this point of view, the conversion efficiency of the laser beam in converting optical energy to thermal energy is the most important factor in anastomosis using optical energy. Therefore, it is very important to use a laser beam having a large absorption coefficient with respect to organic tissue and water. For example, a carbon dioxide laser is known to have an absorption coefficient which is more than 1000 times that of the YAG laser. In organic tissue, all energy components of a carbon dioxide laser are converted to thermal energy at a depth of 0.1 mm from the skin surface. Therefore, when a carbon dioxide laser is used, a blood vessel can be anastomosed from the vicinity of the outer layer of the blood vessel without damaging the inner and intermediate layers. The carbon dioxide laser is expected to greatly improve the anastomosis effect. In addition to this advantage, unlike the YAG laser beam, the carbon dioxide laser has no restriction on the focal length, thereby improving operational procedures.

FIG. 2 is a graph showing the laser beam density as a function of the beam spot so as to explain the possible anastomosis conditions when a blood vessel having a diameter of less than 1 mm is anastomosed with a carbon dioxide laser. In this case, the scanning rate is 0.6 mm/sec, the lens is a ZnSe meniscus lens, and the incident beam spot diameter is 6 mm. Since capillary anastomosis is generally performed under microscopic observation, a practical focal length range is 5 to 30 cm. In the example shown in FIG. 2, when the focal length is 6 cm, the converged beam spot diameter is 0.1 mm. Under these conditions, an obtainable anastomosis energy or power density falls within the range of 1.9 to 4.5 $W/mm^2$, which can be calculated to correspond to a laser beam energy range of 15 to 35 mW. However, when the focal length is 25 cm, the converged beam spot diameter is about 0.3 mm, and an obtainable anastomosis power density falls within the range of 0.8 to 1 $W/mm^2$, which can be calculated to correspond to a laser beam energy range of 55 to 75 mW. As is apparent from the above description, when the converged beam spot diameter is increased, the obtainable anastomosis energy density falls within a narrower range, so that stricter control of the laser beam is required. Furthermore, the above conditions greatly vary in accordance with the type of blood vessel or its state. A small optical output must be accurately and precisely controlled at each application. Therefore, a carbon dioxide laser vascular anastomosis apparatus must inevitably satisfy the following conditions:

(1) an optical system having a long focal length of not less than 10 cm
(2) a small converted beam spot diameter of about 0.1 mm, and
(3) highly precise control of an optical output of not more than 100 mW.

A high-power cutter and a laser knife are known as typical examples of a carbon dioxide laser application. These apparatuses require a high-power laser of 10 to 100 W or higher. However, the vascular anastomosis apparatus of the present invention requires laser energy which is 1/1000 that of the high-power laser described above. Therefore, a very low-power laser energy required for the apparatus of the present invention must be achieved with an entirely new concept.

The conventional drawbacks are described as follows.

When a capillary having a diameter of not more than 1 to 2 mm is subjected to vascular anastomosis, the laser spot must be located within the microscopic range of view of the microscope since capillary anastomosis must be performed under microscopic observation. However, in the conventional manipulator system or the conventional optical fiber system, the manipulator or optical fiber must be located in the vicinity of the object to be examined, even when the focal length of the laser beam is as short as 1 to 2 cm, thereby interfering with the view through the microscope. However, when the focal length of the laser knife apparatus is increased (i.e., is 10 cm or longer), a beam spot having a diameter of 0.1 to 0.2 mm or less required for capillary anastomosis cannot be obtained due to diffraction. These conventional drawbacks result from the fact that a laser beam having a considerably small beam (e.g. having a beam diameter of several millimeters) is incident on the focusing lens in the conventional laser knife apparatus. This can be analyzed from the optics as follows.

When the diameter of the laser beam spot is given as a, the focal length of the focusing lens is given as f, and the wavelength of the laser beam is given as $\lambda$, a diameter b of the laser beam spot at the focal point is given as $b = 4\lambda f/a\pi$ due to the diffraction phenomenon, even if the focusing lens is assumed to have no aberration. When the carbon dioxide laser is used, the focal length f is typically about 6 cm and the laser beam spot diameter a is typically about 6 mm in the conventional laser knife apparatus. Therefore, when the wavelength form $\lambda$ is 10.6 $\mu$m, the spot diameter b becomes 0.1 mm. In this case, the spot diameter b falls within the possible operation beam spot diameter range of 0.1 to 0.3 mm. When the focal length f is equal to or greater than 20 cm so as to perform anastomosis under microscopic observation, the spot diameter b becomes about 0.4 mm. As a result, this diameter falls outside the possible operation beam spot diameter range, as shown in FIG. 2. Therefore, when the laser beam guided through the optical fiber is converged, no possible operation beam spot diameter can be obtained, since the diameter a is less than 1 mm.

As far as the energy density is concerned, the possible operation beam range corresponds to a very low power optical output range. For example, when the focal length f is 6 cm, an energy density falls within the range of 2 to 4.5 W/mm$^2$. This energy density corresponds to a laser output of 15 to 35 mW. In the conventional laser knife, an incision, an evaporation process, and the like are performed in a laser power range of 10 to 100 W. When the high-power laser discharge tube is controlled to produce a small discharge current so as to obtain the anastomosis range, the discharge current must be decreased to fall within the range of 0.1 to 1 mA. In general, the discharge tube has a high impedance and often tends not to be controlled. Therefore, it is very difficult to perform anastomosis with the conventional laser knife.

SUMMARY OF THE INVENTION

It is, therefore, a principal object of the present invention to provide a vascular anastomosis apparatus provided with a visible guide light beam having a converging point coinciding with that of a carbon dioxide laser beam which has a focal length of not less than 10 cm, which has a spot diameter of not more than 0.1 to 0.3 mm and which has a power falling within the range of 10 mW to 1 W.

It is another object of the present invention to provide a vascular anastomosis apparatus as a single unit which provides a stable output range varying from a low power output to a high power output, and which can be used together with a laser knife.

In order to achieve the above objects of the present invention, there is provided a vascular anastomosis apparatus comprising: carbon dioxide laser means; optical means for collimating a laser beam from said carbon dioxide laser means so that a collimated laser beam has a large beam spot, and for converging the collimated laser beam; means for emitting a visible guide light beam having the same converging point or optical axis as that of the laser beam; and means for detecting part of the laser beam and for controlling a laser output from said carbon dioxide laser means.

According to the vascular anastomosis apparatus of the present invention, anastomosis can be completed in a few minutes as compared with conventional suturing wherein it takes one hour or longer to suture a blood vessel with a needle and thread, so that the organic tissue can quickly and safely recover.

Other objects, features and advantages of the present invention will become apparent from the following detailed description taken in conjunction with the accompanying drawings.

BRIEF DESCRIPTION OF THE DRAWINGS

FIG. 14 is a bar graph showing the success rate of the experiments.

DETAILED DESCRIPTION OF THE PREFERRED EMBODIMENTS

Before describing the preferred embodiments of the present invention, basic assumptions regarding a long focal length, a small spot diameter, and visual analysis of an accurate focal point necessary to obtain good anastomosis effects are described.

Figure 1:
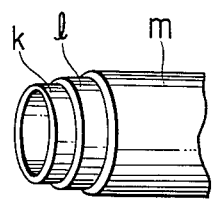
FIG. 1 is a representation of the structure of a blood vessel.
Figure 3:
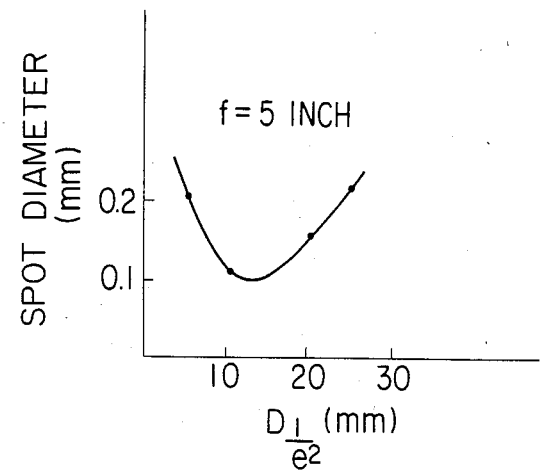
FIG. 3 is a graph for explaining the relationship between the beam spot diameters of the input and output laser beams with respect to the focusing lens.
Figure 2:
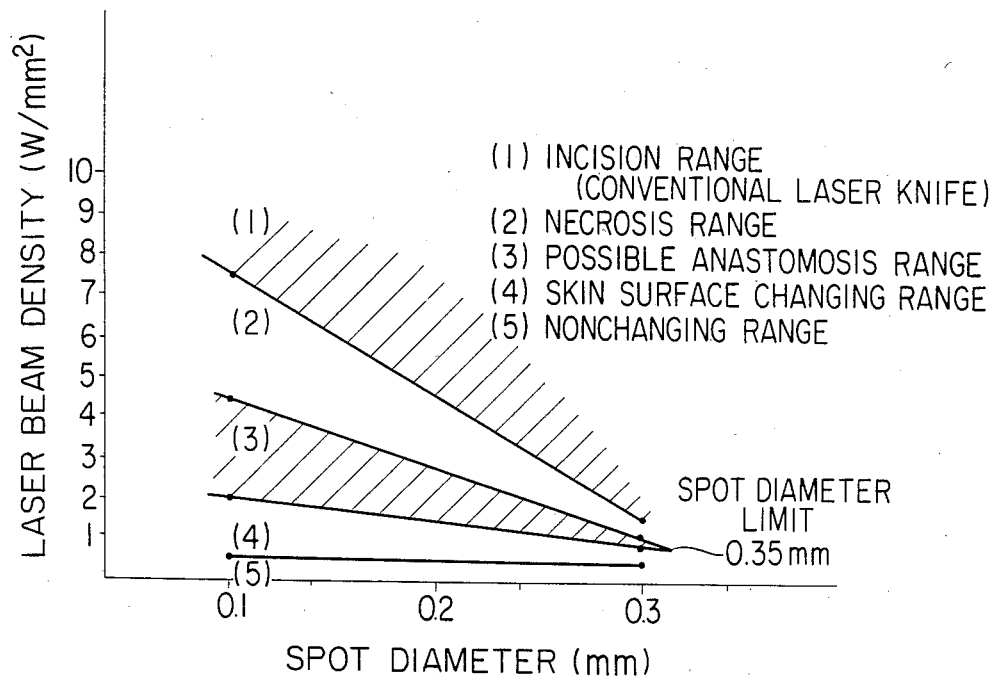
FIG. 2 is a graph for explaining the conditions for vascular anastomosis using a carbon dioxide laser.

A ratio $\lambda/a$ must be small to obtain a small spot diameter when $f \gtrsim 20$ cm. As previously described, the wavelength $\lambda$ cannot be decreased to minimize the damage to the organic tissue. Therefore, in practice, the input laser beam spot diameter a must be increased. The focusing lens has a given aberration characteristic, so that the beam spot is spread to some extent. The aberration characteristic is associated with the material and shape of the lens. The actual beam spot diameter is a sum of a diameter obtained by the diffraction limit and a spread portion caused by the aberration characteristic described above. FIG. 3 shows the relationship between the incident beam spot diameter of the lens and the spot diameter when a ZnSe meniscus lens having a focal length $f=5$ inches is used. $D_1/e^2$ must fall within the range of 12 to 20 mm to satisfy the condition $b=0.1$ mm. An optical output up to 1 W is required as the anastomosis laser power, so that the discharge tube has a length of about 10 cm, or the resonator has a length of 20 cm. In order to obtain a beam spot represented by $D_1/e^2$ falling within the range of 12 to 20 mm, a minimum diameter of a window must fall within a range from 18 to 30 mm. Although such a diameter is desirable, since the resonator length is short, a higher order transverse mode also occurs. As a result, a spot diameter for anastomosis cannot be obtained. According to an experiment conducted, even when the resonator length was 100 cm, a higher order mode occurred when the window diameter was 15 mm or more. Therefore, a sufficiently small diameter (e.g., about 5 mm) must be used to emit a laser beam so as to obtain a single transverse mode. Thereafter, the beam diameter is increased by an optical system for increasing the spot diameter. The laser beam having an enlarged diameter is incident on the focusing lens, thereby obtaining a beam spot suitable for anastomosis.

On the other hand, when the carbon dioxide laser is used to perform vascular anastomosis, this laser is an infrared ray and cannot be visually seen. Therefore, a guide light beam is used to know a spot position of the carbon dioxide laser in advance.

Furthermore, the success/failure of anastomosis greatly depends on the spot diameter, so that the focal point of the carbon dioxide laser beam must coincide with that of the guide light beam.

The preferred embodiments of the present invention will be described with reference to the accompanying drawings.

Figure 4:
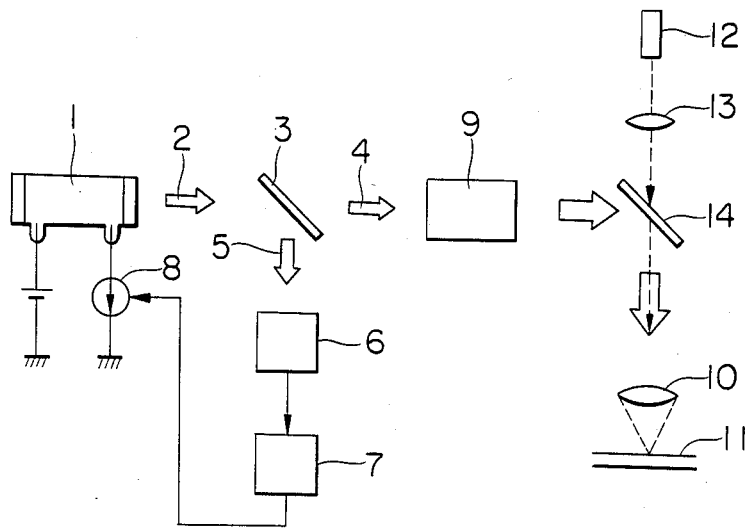
FIG. 4 is a diagram of a vascular anastomosis apparatus according to a first embodiment of the present invention.

FIG. 4 is a diagram of a vascular anastomosis apparatus according to a first embodiment of the present invention. A laser beam 2 emitted from a carbon dioxide laser tube 1 is split by a beam splitter 3 into an operation beam 4 and a monitor beam 5 used for laser output control. The operation beam 4 has a diameter of only a few millimeters, so its diameter is enlarged by a beam expander 9. The expanded beam is focused by a focusing lens 10 and irradiates a portion 11 to be examined. In this case, when ZnSe, NaCl, KCl or the like is used as a material of the focusing lens 10, this material can transmit both the carbon dioxide laser and visible light therethrough, so that the optical axis of a visible light laser 12 such as a HeNe laser can be aligned with that of the carbon dioxide laser at a reflecting mirror 14. As a result, the operation beam spot can be monitored with respect to the portion 11. The light-receiving surface of the reflecting mirror 14 is coated with a dielectric coating or indium oxide coating whose impurity content is controlled, so that the reflecting mirror 14 can reflect infrared rays. The anastomosis operation can be performed under microscopic observation, so that the laser spot is properly tracked together with the visible guide beam with respect to the portion 11. A refractive index of the focusing lens 10 with respect to the carbon dioxide laser beam is different from that with respect to light from the visible light laser 12. In order to correct this, a correction lens 13 is inserted between the visible light laser 12 and the reflecting mirror 14.

Since the anastomosis laser power range is so limited as previously described with reference to the conventional laser knife, the laser output must be precisely controlled. For this purpose, the monitor beam 5 split by the beam splitter 3 is incident on a photosensor 6. The photosensor 6 practically comprises a thermopile element or a pyroelectric element. The photosensor 6 must have high precision, allowing only a 1% tolerance with respect to a laser output range of 10 mW to 1 W. The energy of the monitor beam 5 incident on the photosensor 6 is substantially equal to or greater than that of the operation beam 4, so that the photosensor 6 has a great thermal inertia. Therefore, an output from the photosensor 6 is processed by a signal processor 7 and is fed back to a discharge current control circuit 8 for controlling the laser discharge tube by varying the current flow between the laser electrodes so that the output of photosensor 6 is maintained constant.

Figure 5:
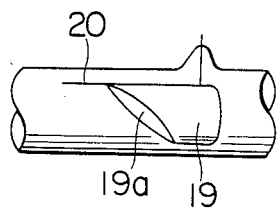
FIG. 5 is a perspective view of an electrode used in the vascular anastomosis apparatus of the present invention.

A low-power carbon dioxide laser can be used in the vascular anastomosis apparatus. However, when the apparatus is used as a laser knife apparatus, a high-power laser can be used. However, when the vascular anastomosis apparatus is used as a laser knife, and the discharge element generally has a large area, a low discharge operation for the high-power laser discharge tube cannot be stably performed. In order to stably perform cathode glow discharge in a DC discharge tube having a cylindrical cathode, an electrode 19 is used as shown in FIG. 5. The cathode electrode 19 has a tilt portion 19a at an end of a cylindrical body which is located on the side of the cathode electrode adjacent the anode (not shown) and a needle portion 20 at the distal end of the tilt portion 19a. In this case, stable discharge operation from a very small current region (i.e., a discharge current of 0.1 mA or less) to a large current region can be performed. In a small current region, a current component is received at the distal end of the needle portion 20. When the current is increased, the discharge area is expanded to the proximal portion of the needle portion 20. When a large current flows, the discharge is performed using the entire portion of the electrode.

Another advantage of the electrode shown in FIG. 5 lies in that sufficiently stable discharge can be performed at a very small current region (i.e., the threshold of the laser resonator). Before main discharge is performed, a current which is smaller than the laser oscillation current continuously flows through the electrodes. Whenever main discharge is required, the current level is switched for main discharge. With this arrangement, optimal transient response characteristics can be obtained, so that power switching is performed to slightly increase or decrease the laser power. This switching cannot be properly implemented with a mechanical shutter.

The signal processor 7 performs sequence control and operations such as differential, integral and proportional calculations of a signal having a level deviated from the predetermined level. When glow discharge is not stably performed, the impedance of the discharge tube greatly varies, and an impulse-like disturbance occurs in the signal processor 7. This results in a transient change in the control system as a whole. When the vascular anastomosis apparatus of the present invention is also used as a laser knife and the laser beam having a power in the range from 10 mW to 20 W is monitored by a beam splitter having a split ratio of about 10%, the monitor beam has a power in the range from 1 mW to 2 W. A conventional thermocouple cannot provide a monitor beam having a tolerance of below 1%. In this case, two beam splitters are used wherein one beam splitter has a split ratio (10:1) and the other beam splitter has a split ratio (1:10). These two beam splitters are switched in accordance with the low- and high-power laser beams, thereby obtaining the desired result.

The monitor beam processing section when the vascular anastomosis apparatus of the present invention is also used as a laser knife apparatus will be described in detail later.

Figure 6:
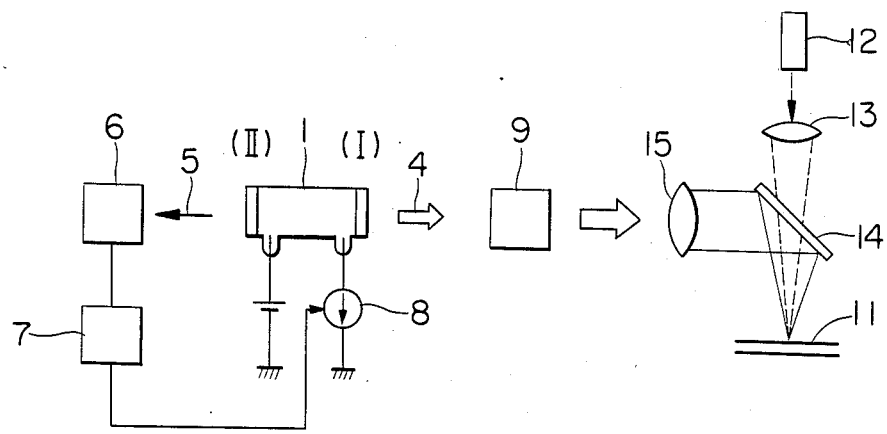
FIG. 6 is a diagram of a vascular anastomosis apparatus according to a second embodiment of the present invention.

FIG. 6 is a diagram of a vascular anastomosis apparatus according to a second embodiment of the present invention. The same reference numerals as used in the first embodiment denote the same parts in the second embodiment. A monitor beam 5 is split by a partially reflecting mirror having a surface (II) which opposes the operation beam output surface (I) and which is treated with a coating such that 90% of incident light beams are reflected and 10% thereof are transmitted. In this manner the monitor beam 5 is emitted from the laser tube. According to this system, an expensive beam splitter need not be used, and alignment of the optical axis can be easily performed. Furthermore, referring to FIG. 6, a focusing lens 15 is disposed in front of a reflecting mirror 14. This construction is effective when a material of the focusing lens 15 comprises germanium, which is non-transparent to visible light. In general, a germanium lens has good focusing characteristics compared with a ZnSe lens. A germanium lens is used whenever anastomosis cannot be performed with a ZnSe lens. In this case, a focusing lens 13 serves as a lens for coinciding the focal point of the visible light beam from the visible light laser 12 with the infrared ray from the focusing lens 15.

Figure 7:
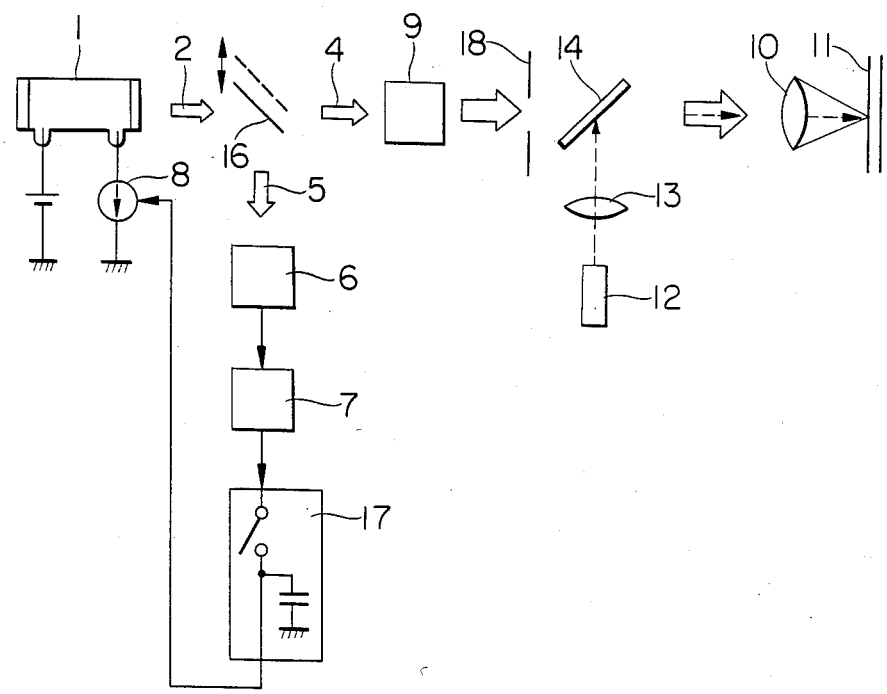
FIG. 7 is a diagram of a vascular anastomosis apparatus according to a third embodiment of the present invention.

FIG. 7 is a diagram of a vascular anastomosis apparatus according to a third embodiment of the present invention. Instead of the beam splitter (FIG. 4) and the partially reflecting mirror (FIG. 6), a shutter 16 consisting of a full reflection mirror for switching the optical paths is used to select one of an operation beam 4 and a monitor beam 5. In general, the laser beam is emitted for only a few seconds to complete each radiation cycle. Laser output variations consist of a change in stability of the reflecting mirror in accordance with a change in ambient temperature, a change in gas pressure, a change in temperature of cooling water. These changes occur for a long period of time. Therefore, when operation is performed with the operation beam 4 by opening the shutter 16 when required, the entire small laser output can be monitored, thereby providing good controllability. Since an input 5 to a photosensor 6 disappears when the shutter 16 is opened, a holding circuit 17 must be connected to the output terminal of a signal processor 7 so as to hold the immediately preceding charge. According to this system, the beam splitter and the partially reflecting mirror need not be used, thus resulting in low cost. Referring to FIG. 7, reference numeral 14 denotes a reflecting mirror obtained by forming a visible light reflection coating on an infrared transmitting base. Reference numeral 18 denotes an aperture or window for controlling the diameter of the carbon dioxide laser beam incident on the focusing lens 10. The window 18 is adjusted to obtain a minimum converging beam diameter in accordance with a given focal length. The window 18 may be mounted in the resonator in a laser having an external mirror.

Problems and countermeasures thereto when the vascular anastomosis apparatus is also used as a laser knife apparatus will now be described.

The laser knife requires a laser output of 1 W to several tens of watts, while the vascular anastomosis apparatus requires a laser output of 5 to 100 mW. In this manner, the power required for the laser knife greatly differs from the power required for vascular anastomosis. Therefore, in general, a laser knife apparatus and a vascular anastomosis apparatus are separately provided.

However, when a series of operations is to be performed (e.g., when incision and anastomosis are alternately repeated), it is preferred that these operational procedures are performed by a single apparatus. However, when the laser output varies from the order of milliwatts to the order of 10 W, the following problems are presented.

In general, the vascular anastomosis apparatus is arranged such that a laser output emitted from the laser oscillator is split into an operation beam and a monitor beam, and that the monitor beam is detected to control the laser output from the laser oscillator. Assume that a split ratio of the monitor beam to the operation beam is 1:10. Under this assumption, when the operation beam has a power of 10 mW to 10 W, the monitor beam has a power of 1 mW to 1 W. Laser power of the order of milliwatts can be easily detected by a highly-sensitive thermopile or pyroelectric element. Therefore, the operation beam having the order of 10 mW can be stably controlled. However, when the operation beam has a power of about 10 W, the photosensor receives a beam having a power of 1 W, and the highly-sensitive sensor is burned out. It is generally impossible for a single photosensor to continuously control the laser beam power across a range of 1 mW to several tens of watts.

In order to solve this problem, two beam splitters are used wherein the first beam splitter has a split ratio (1/10) and the second beam splitter has a split ratio (10/1). When a high-power laser beam is selected by the physician, the first beam splitter is used. Otherwise, the second beam splitter is used. Therefore, the energy or power range of the monitor laser beam is narrowed, so that a single photosensor can detect the power of the monitor beam.

Figure 8A:
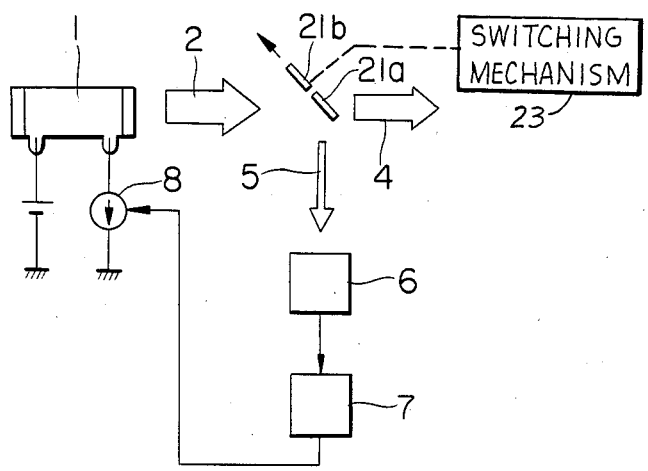
FIGS. 8A and 8B are respectively diagrams of a vascular anastomosis apparatus according to a fourth embodiment of the present invention.
Figure 8B:
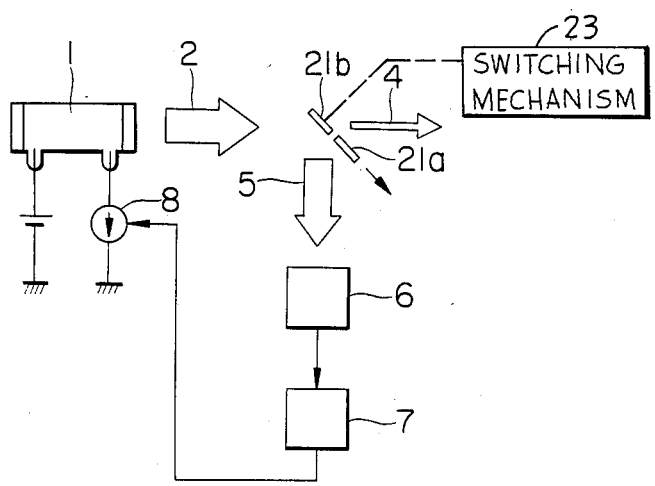

FIGS. 8A and 8B are diagrams showing a vascular anastomosis apparatus according to a fourth embodiment of the present invention. A beam splitter comprises a ZnSe partially reflecting mirror 21a having a transmittance of 9/10 and a ZnSe partially reflecting mirror 21b having a transmittance of 1/10. A photosensor 6 comprises a thermopile element. Control of the laser output is performed by controlling a discharge current. In the vascular anastomosis apparatus having the construction described above, when a relatively high output is required as an operation beam 4, a switching mechansim 23 positions the partially reflecting mirror 21a having the larger transmittance across the beam path, as shown in FIG. 8A. However, when a relatively low laser output is required, the partially reflecting mirror 21b having the smaller transmittance is set across the beam path, as shown in FIG. 8B. When a stable laser beam 2 is emitted from the laser tube 1 at a power in the range from 1 to 10 W and the partially reflecting mirror 21a is set, the laser knife beam 4 having a power of 0.9 to 9 W is obtained. However, when the beam splitter is switched to the reflecting mirror 21b, the vascular operation beam 4 having a power of 0.1 to 1 W can be obtained. In this manner, radiation beams varying from the lower power to the higher power can be obtained. Furthermore, the monitor beam 5 has a relatively high power, so that the S/N ratio of the photosensor 6 will not be degraded.

Figure 9:
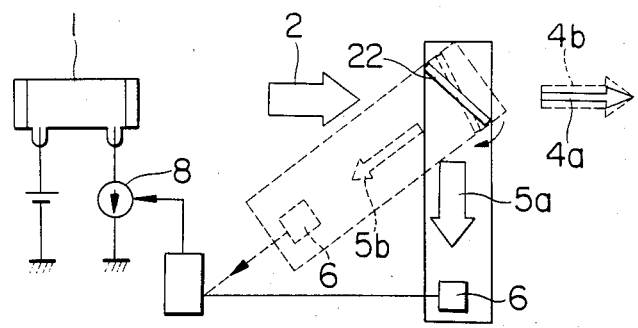
FIG. 9 is a diagram showing part of a vascular anastomosis apparatus according to a fifth embodiment of the present invention.

When the laser beam emitted from the laser tube is deflected, the laser beam can be controlled in accordance with a vascular anastomosis apparatus of a fifth embodiment of the present invention, as shown in FIG. 9, a pivot mechanism is disposed in a beam splitter 22 so as to change an incident angle of a laser beam 2 with respect to the beam splitter 22 in accordance with a desired output, thereby changing a transmittance (reflectance). Referring to FIG. 9, if a vascular operation beam 4a having a low power is required, the reflectance is increased such that the tilt angle (indicated by the solid line) with respect to the optical axis of the beam splitter 22 is greater than Brewster's angle, thereby increasing the power of a monitor beam 5a. However, when a laser knife beam 4b having a relatively high power is required, the tilt angle with respect to the optical axis of the beam splitter 22 comes closer to the Brewster's angle, as indicated by the dotted line, thereby decreasing the power of a monitor beam 5b. In this case, the photosensor 6 is interlocked with pivotal movement of the beam splitter 22, so that the monitor beams 5a and 5b can be incident on the photosensor 6 regardless of the angle of the beam splitter 22.

However, unlike the above arrangement wherein the beam splitter 22 is interlocked with the photosensor 6, a plurality of sensors may be arranged such that any one of the sensor receives light reflected from the beam splitter 22.

By changing the transmittance (reflectance) of the beam splitter, the laser oscillator can be oscillated in a stable range. Furthermore, the laser oscillator can be oscillated in a range so as not to decrease the S/N ratio of the photosensor, thereby obtaining a stable laser output at a given power.

In the fourth embodiment (FIGS. 8A and 8B), two beam splitters respectively having predetermined split ratios must be prepared, resulting in relatively high cost. Another arrangement of a monitor beam process will be described when the output varies power in a side range.

Figure 10:
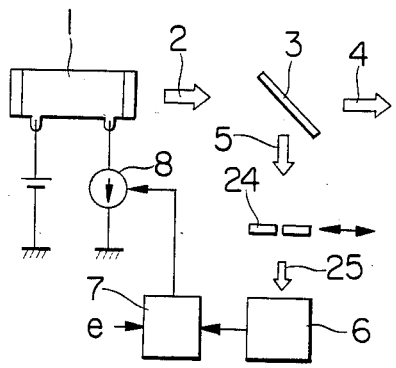
FIG. 10 is a diagram showing part of a vascular anastomosis apparatus according to a sixth embodiment of the present invention.

FIG. 10 is a vascular anastomosis apparatus according to a sixth embodiment of the present invention wherein an optical energy limiter 24 or optical attenuator is detachably arranged at a light incident port of a photosensor 6 for detecting the energy level of the monitor beam. When the energy of the monitor beam 5 is relatively high, the optical energy limiter 24 is inserted in the incident port of the photosensor 6 so as to decrease the energy of the beam incident on the photosensor 6. A detection signal from the photosensor 6 is compared by a signal processor 7 with a reference signal e, and a comparison output is fed back to a discharge current control circuit 8.

Figure 11:
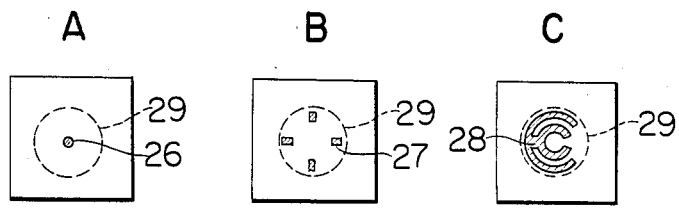
FIG. 11 shows optical energy limiters.

FIGS. 11A, 11B and 11C show types of structure of the optical energy limiter, respectively. Referring to FIG. 11A, a ratio of an area of a circular hole 26 to that of a light-receiving portion 29 for receiving the monitor beam 5 is defined as an optical energy limiting ratio. Referring to FIG. 11B, a ratio of a total area of rectangular holes 27 to that of a light-receiving portion 29 is defined as an optical energy limiting ratio. Similarly, referring to FIG. 11C, a ratio of a total area of a substantially concentrical hole to that of a light-receiving portion 29 is defined as an optical energy limiting ratio. The optical energy limiter is not limited to the structures shown in FIGS. 11A to 11C. For example, a partially transmitting mirror or optical chopper may be used to obtain the same effect.

Even if the beam splitter 3 has a fixed split ratio (monitor beam:vascular operation beam or laser knife beam=1:10), the optical energy limiter 24 is inserted for a high power laser output, thereby obtaining a low energy detection beam 25. Otherwise, the optical energy limiter 24 is not used, and the monitor beam 5 is directly detected. In this arrangement, only one beam splitter is used, and a low energy highly-sensitive photosensor can be used at low cost.

Figure 12:
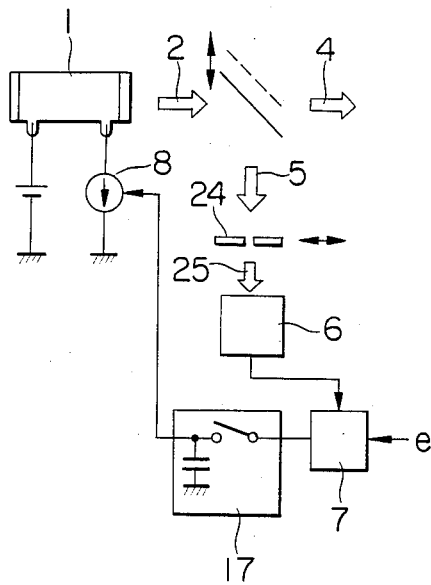
FIG. 12 is a diagram showing part of a vascular anastomosis apparatus according to a seventh embodiment of the present invention.

FIG. 12 is a vascular anastomosis apparatus according to a seventh embodiment of the present invention. In this embodiment, a shutter 16 comprising a full reflection mirror is used in place of the beam splitter. The shutter 16 is removed from the optical path of the laser beam while a surgical operation is being performed, and an output laser beam 2 is used as an operation beam 4. However, while no surgical operation is being performed, the shutter 16 is inserted in the optical path to reflect all of the laser beam 2, and the reflected laser beam is used as a monitor beam 5. In general, the radiation time of the laser beam is short, so that a stable discharge current immediately before irradiation is maintained to be the current at the time of irradiation (i.e., in the nonmonitor mode). For this purpose, in the same manner as in FIG. 7, a holding circuit 17 is inserted between a signal processor 7 and a discharge current control circuit 8.

Since the optical energy limiter 24 is detachable in accordance with the level of the laser output, the laser output can be detected by a small energy photosensor, and an expensive beam splitter need not be used.

Figure 13:
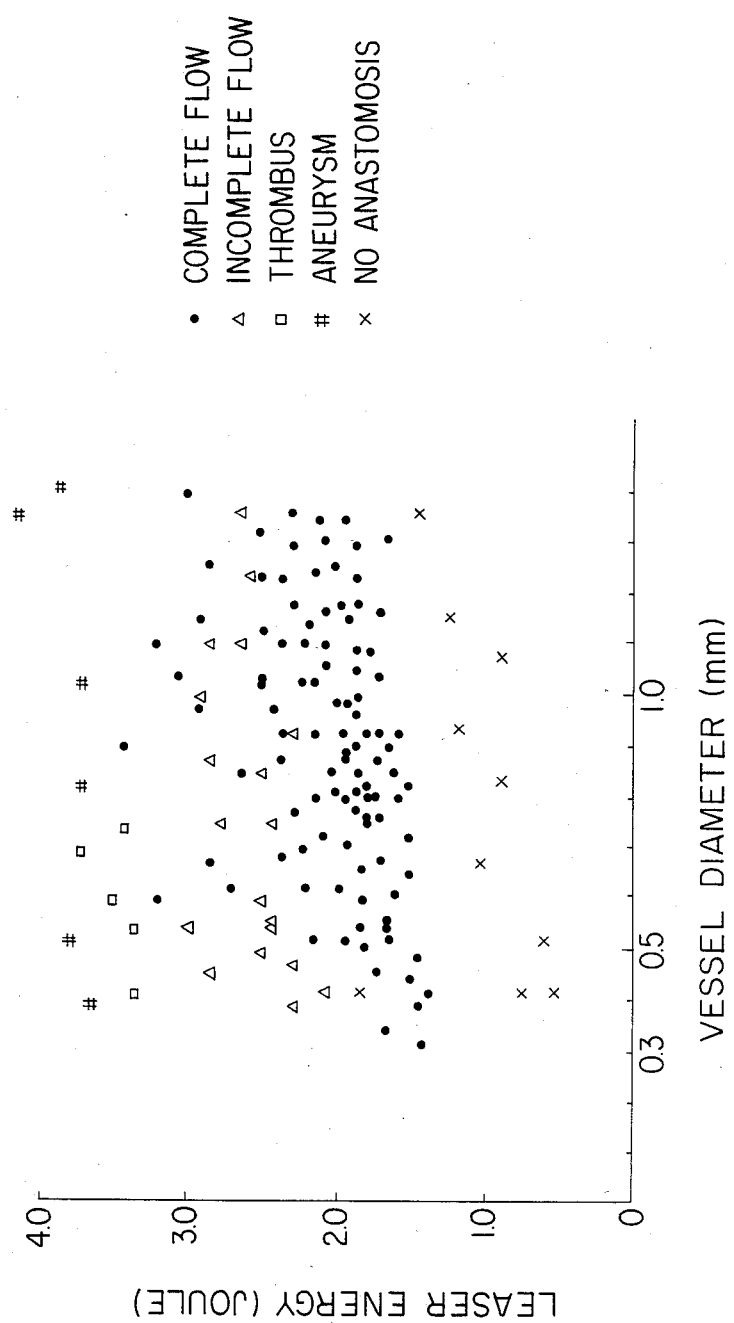
FIG. 13 is a graph showing experimental results when the vascular anastomosis apparatuses of the present invention are used.

The anastomosis experimental results using the apparatus of the present invention are described. FIG. 13 shows the results when arteries of rats were cut and then anastomosed. 135 experimental anastomosis operations were performed. Among them all, anastomosis operations were successful when a laser beam having an energy level of 1.5 to 3 Joule was used to irradiate blood vessels having diameters which fell within the range of 0.3 mm to 1.4 mm. FIG. 14 shows the success rate of the operations. When a laser beam having an energy level of 1.5 to 3 Joule was used, it was found that 100% of operations were successful. Unlike conventional suturing wherein one blood vessel takes one hour or longer to suture, the vascular anastomosis apparatus of the present invention allows the physician to perform the identical operation in a few minutes. Furthermore, the anastomosed portion can properly and safely recover.

The anastomosis operation with the vascular anastomosis apparatus can be applied to other surgical operations relating to nerves and internal organs.

According to the present invention as described above, a vascular anastomosis apparatus can be provided which satisfies three conditions: the proper focal length required for a surgical operation under microscopic observation; a small beam spot; and a lower power laser beam. According to this apparatus, vascular anastomosis can be properly and safely performed within a short period of time.

The conventional problem which fails to provide a laser output varying over a wide power range can be overcome. Therefore, the apparatus of the present invention can achieve both vascular anastomosis and laser knife operation.

What is claimed is:

1. A vascular anastomosis apparatus, comprising:
   carbon dioxide laser means comprising a gas laser tube for emitting a laser beam from one end thereof, said gas laser tube having longitudinally spaced anode and cathode electrodes therein,
   said cathode electrode having a first end relatively proximate to said anode and a seond end relatively remote from said anode, with a needle portion at said first end thereof,
   said cathode electrode having a tilt portion adjacent said needle portion, said tilt portion having an electron emission surface the area of which increases with increasing distance from said anode;
   optical means for (i) collimating said laser beam emitted from one end of said gas laser tube so as to obtain a collimated operation laser beam having a relatively large beam diameter and for (ii) converging the collimated operation laser beam upon a desired area;
   means for emitting a visible guide beam;
   optical path control means for spatially synchronizing said collimated operation laser beam and said visible guide beam so that the guide beam illuminates the area upon which the laser beam is converged;
   means for extracting from said laser beam a monitor laser beam the intensity of which is dependent upon the intensity of said laser beam; and
   laser output controlling means, including a photosensor for detecting the monitor laser beam, for regulating the intensity of the laser beam output of said carbon dioxide laser means,
   whereby a blood vessel may be anastomosed with the operation laser beam by converging the collimated operation laser beam on a desired area of said blood vessel.

2. An apparatus according to claim 1, wherein said means for extracting the monitor laser beam comprises a beam splitter for splitting the laser beam from the one end of said gas laser tube into the operation laser beam and the monitor laser beam.

3. An apparatus according to claim 2, wherein said beam splitter comprises splitting ratio changing means for splitting the laser beam into the operation laser beam and the monitor laser beam in varying ratios.

4. An apparatus according to claim 3, wherein said splitting ratio changing means comprises a plurality of partially reflecting mirrors having different transmittances (reflectances) and a switching mechanism for selecting one of said partially reflecting mirrors in accordance with a predetermined output.

* * * * *